United States Patent [19]

Schnatterer et al.

[11] Patent Number: 5,130,493
[45] Date of Patent: Jul. 14, 1992

[54] PROCESS FOR THE PREPARATION OF O-HYDROXY-BENZALDEHYDES

[75] Inventors: Albert Schnatterer; Helmut Fiege, both of Leverkusen; Karl-Heinz Neumann, St. Augustin, all of Fed. Rep. of Germany

[73] Assignee: Bayer Aktiengesellschaft, Leverkusen, Fed. Rep. of Germany

[21] Appl. No.: 681,244

[22] Filed: Apr. 5, 1991

[30] Foreign Application Priority Data

Apr. 13, 1990 [DE] Fed. Rep. of Germany ....... 4012008

[51] Int. Cl.$^5$ ............................................. C07C 45/36
[52] U.S. Cl. .................................. 568/432; 568/431; 568/433
[58] Field of Search ...................... 568/431, 432, 433

[56] References Cited

U.S. PATENT DOCUMENTS

| 4,429,163 | 1/1984 | Nishizawa et al. | 568/432 |
| 4,453,016 | 5/1984 | Au et al. | 568/432 |
| 4,471,140 | 9/1984 | Au | 568/432 |
| 4,481,374 | 11/1984 | Christidis | 568/432 |
| 4,772,754 | 9/1988 | Rohrscheid | 568/432 |
| 4,929,766 | 5/1990 | Campo | 568/432 |

FOREIGN PATENT DOCUMENTS 0012939 7/1980 European Pat. Off. ............ 568/431

*Primary Examiner*—Werren B. Lone
*Attorney, Agent, or Firm*—Sprung Horn Kramer & Woods

[57] ABSTRACT o-Hydroxy-benzaldehydes can be obtained by oxidation of the o-cresols, on which they are based, with oxygen in the presence of substances having a base reaction in a solvent if chelate complexes of iron, manganese or a mixuture of both with polyaza-macrocycles as chelating agents are employed as catalysts. Copper or a copper compound is advantageously added as a co-catalyst.

11 Claims, No Drawings

PROCESS FOR THE PREPARATION OF O-HYDROXY-BENZALDEHYDES

BACKGROUND OF THE INVENTION

1. Field of the Invention

The invention relates to a process for the preparation of o-hydroxy-benzaldehydes by catalytic oxidation of the o-cresols, on which they are based, with oxygen in the presence of chelate complexes of iron, manganese or a mixture of both.

o-Hydroxy-benzoldehydes are important intermediates for industrial syntheses of perfumes, dyestuffs, pharmaceutical, plant protection agents and photographic chemicals. The most important representative industrially is salicylaldehyde. It is used, inter alia, as a starting material for the preparation of coumarin.

2. Description of the Related Art

Salicylaldehyde is industrially accessible in several ways. The starting material is either phenol or o-cresol (Ullmanns Encyklopädie der Technischen Chemie, (Ullmann's Encyclopedia of Industrial Chemistry) 5th Edition, volume A3 (1985), p. 470). An isomer mixture of o-hydroxy- and p-hydroxy-benzaldehyde is formed in the Reimer-Tiemann reaction of phenol with chloroform in the presence of alkali (U.S. Pat. No. 3,365,500, EP-68,725). The formation of the p-hydroxy isomer is avoided by a process in which, in a first step, phenol in the form of the boric acid ester is selectively hydroxymethylated in the o-position with formaldehyde. After the cleavage of the boric acid ester, the o-hydroxy-benzyl alcohol is oxidised in a further step to salicylaldehyde with oxygen in the liquid phase on a platinum contact (DE-AS (German Published Specification) 1,261,517, DE-OS (German Published Specification) 2,612,844). Starting from o-cresol, salicylaldehyde can be prepared by side-chain chlorination and hydrolysis of the dichloromethyl group to the aldehyde group. In this process the hydroxy group has to be protected by esterification JP-73/03831, cited by C.A. 79(1973), 18387x). Further processes are based on the electrochemical reduction of salicylic acid (Ind. Chemist 39(1963), 238-41, cited by C.A. 59(1963), 10986b) and the catalytic reduction of salicyloyl halides (JP-68/13204, cited by C.A. 70 (1969), 28646j.).

The processes until now have the disadvantage that they either yield isomer mixtures or else are complicated multi-step processes in which, for example, auxiliaries such as boric acid or auxiliaries for the protection of reactive functional groups on the substances to be reacted are required.

According to EP-12,939, p-cresol derivatives can be oxidised to the corresponding p-hydroxy-benzaldehydes with oxygen in the liquid phase int eh presence of a base and of a cobalt compound in reasonable yields. This specification at the same time points out that o-cresol cannot be oxidised in this way.

SUMMARY OF THE INVENTION

A process for the preparation of o-hydroxy-benzaldehydes of the formula

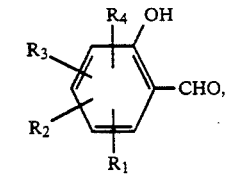

in which $R_1$, $R_2$, $R_3$ and $R_4$ independently of one another denote hydrogen, straight-chain or branched $C_1$–$C_{10}$-alkyl, $C_3$–$C_8$-cycloalkyl, straight-chain or branched $C_1$–$C_{10}$-alkoxy, phenyl or halogen, where alkyl or cycloalkyl may only be in the p-position to the hydroxyl group if they carry no a-H-atoms, by catalytic oxidation of o-cresols of the formula

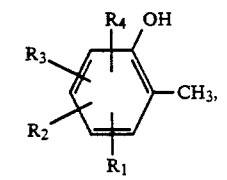

in which $R_1$–$R_4$ have the meaning indicated, with oxygen in the presence of substances having a basic reaction and in a solvent has been found, which is characterised in that chelate complexes or iron, manganese or a mixture of both with polyaza-macrocycles as chelating agents are employed as catalysts.

The process according tot he invention offers a crucial advantage compared with the prior art, since it permits the selective preparation of o-hydroxy-benzaldehydes from the o-cresols on which they are based in one reaction step. o-Cresols are compounds which are easily accessible industrially. The use of oxygen as an oxidizing agent represents an optimum, as far as the price and the ecology are concerned.

The selective oxidation of the methyl group in the o-position to the hydroxyl group stops at the stage of the aldehyde group; a further oxidation to the carboxyl group is not observed. The process according to the invention is all the more surprising as the known process for the selective oxidation of p-cresol to p-hydroxy-benzaldehyde using oxygen cannot be used on o-cresols (EP-12,939). If a further methyl group is situated in the second o-position to the hydroxyl group, this is also oxidised to the aldehyde group. Methyl groups int eh m-position to the hydroxyl group are not attacked under the reaction conditions according to the invention.

DETAILED DESCRIPTION OF THE INVENTION $C_1$–$C_{10}$-alkyl can be straight-chain or branched and is, for example, methyl, ethyl, propyl, isopropyl, butyl, isobutyl, tert.-butyl, or one of the isomeric pentyls, hexyls, octyls or decyls.

Apart form the ring C atoms, $C_3$–$C_8$-cycloalkyl can also contain C atoms in the form of 1 or 2 methyl or ethyl substituents and is, for example, cyclopropyl, methylcyclopropyl, dimethyl-cyclopropyl, cyclobutyl, cyclopentyl, cyclopentyl, dimethyl-cyclopentyl, cyclohexyl, methyl-cyclohexyl, dimethyl-cyclohexyl, cyclohexyl or cyclooctyl and also the corresponding cycloalkyl substituted by ethyl.

$C_1-C_{10}$-alkoxy can be straight-chain or branched and is, for example, methoxy, ethoxy, propoxy, isopropoxy, butoxy, isobutoxy, tert.-butoxy, or one of the isomeric pentyloxy, hexyloxy, octyloxy or decyloxy.

Halogen is, for example, fluorine, chlorine or bromine, preferably chlorine or bromine.

Alkyl and alkoxy preferentially have 1-6 C atoms, particularly preferentially 1-4 C atoms. Cycloalkyl preferentially has 3, 5 or 6 atoms, particularly preferentially 5 or 6 C atoms and can be monosubstituted or disubstituted by methyl or ethyl.

Phenyl can be monosubstituted or disubstituted by halogen of the type mentioned and/or by $C_1-C_4$-alkyl of the type mentioned.

Preferentially, o-cresols of the formula

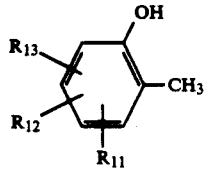
(III)

are employed in which $R_{11}$, $R_{12}$ and $R_{13}$ independently of one another denote hydrogen, straight-chain or branched $C_1-C_6$-alkyl, $C_5-C_6$-cycloalkyl, straight-chain or branched $C_1-C_6$-alkoxy, phenyl or halogen, where alkyl or cycloalkyl may only be in the p-position to the hydroxyl group if they carry non a-H-atoms.

Particularly preferentially, o-cresols of the formula

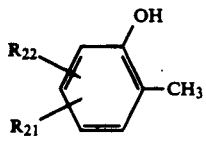
(IV)

are employed in which $R_{21}$ and $R_{22}$ independently of one another represent hydrogen, straight-chain or branched $C_1C_6$-alkyl, cycloalkyl, straight-chain or branched $C_1-C_6$-alkoxy, phenyl or halogen, where alkyl or cyclohexyl may only be in the p-position to the hydroxyl group is they carry no a-H-atoms.

According to the invention, alkyl or cycloalkyl which are in the p-position to the hydroxyl group carry no a-H-atoms. This is the case if the C atom linked directly to the aromatic nucleus is tertiary; examples thereof are the tert.-butyl group and the 1-methylcyclohexyl group.

From the large number of o-cresols which can be employed according to the invention, those which may be mentioned by way of example are: o-cresols, 4-chloro-2-methylphenol, 4,6-dibromo-2-methylphenol, 2,6-dimethylphenol, 2,3-dimethylphenol; the process according to the invention is particularly important for the oxidation of o-cresols.

The process according to the invention is characterised by the use of chelate complexes of iron, manganese or a mixture of both with polyaza-macrocycles as chelating agents. Important representatives of these polyazamacrocycles are the aza-annulenes. An example which may be mentioned of apolyaza-annulene which can be employed according to the invention is 5,14-dihydro[b,i][5,9, 14,18]tetraaza[14]-annulene (Liebigs Ann. Chem. 711 (1968), 137-137).

Particularly important and therefore preferred polyazamacrocycles are porphyrins, phthalocyanines, porphyrinanalogous compounds and those compounds which results from these by chemical modification, for example the chlorins as partially hydrogenated porphyrins. The porphyrins can in this case be of natural origin, for example haematoporphyrin; but they can also be synthetic. The iron, manganese or a mixture of both is preferentially employed in the form of complexes with synthetic macrocycles. These metal complexes are represented by the formula

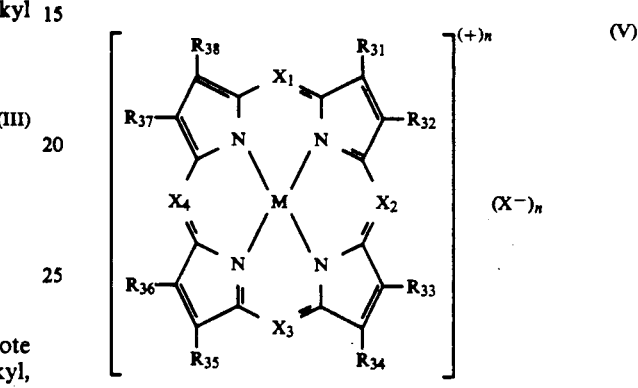
(V)

in which

M denotes iron or manganese $X_1$, $X_2$, $X_3$ and $X_4$ independently represent N or the $CY_1$, $CY_2$, $CY_3$ and $CY_4$ labelled with the same index, where $Y_1$, $Y_2$, $Y_3$ and $Y_4$ independently of one another denote hydrogen, straight-chain or branched $C_1-C_{10}$-alkyl, $C_3-C_8$-cycloalkyl, $C_7-C_{10}$-aralkyl, $C_6-C_{14}$-aryl, which can be partially hydrogenated, or an aromatic or nonaromatic 5- or 6-membered heterocyclic ring system having 1 to 3 heteroatoms form the group comprising N, O and S, $R_{31}$, $R_{32}$, $R_{33}$, $R_{34}$, $R_{36}$, $R_{37}$ and $R_{38}$ independently of one another denote hydrogen, halogen, straight-chain or branched $C_1-C_{10}$-alkyl, $C_3-C_8$-cycloalkyl, $C_7-C_{10}$-aralkyl or phenyl, where the two radicals of a pyrrole ring together with the C atoms substituted by them can form $C_6-C_{14}$-aryl, which can be partially hydrogenated, or an aromatic or nonaromatic 5- or 6-membered heterocyclic ring system having 1 to 3 heteroatoms from the group comprising N, O and S, $X^-$ is an anion equivalent of an inorganic or organic acid, or hydroxyl or alkoxy and n denotes the number zero or one.

Straight-chain or branched $C_1-C_{10}$-alkyl, $C_3-C_8$-cycloalkyl and halogen have the abovementioned scope of meaning. $C_7-C_{10}$-aralkyl is, for example, benzyl, phenyl-ethyl, phenylpropyl or phenyl-butyl, preferably benzyl. $C_6-C_{14}$-aryl is, for example, phenyl, naphthyl, anthryl, phenanthryl or biphenylyl, preferably phenyl or naphthyl. An aryl of this type by definition also includes the ring systems resulting therefrom by partial hydrogenation. In the case of the radicals $R_{31}$ to $R_{38}$ on the pyrrole nuclei, the range thus reaches from the pyrrole system, for example to the isoindole system (3,4-benzo-fused pyrrole), to 3,4-naphthaleno-pyrrole, to 3,4-anthraceno-pyrrole, but also to cyclohexano-pyrrole, to 3,4-anthraceno-pyrrole, but also to cyclohexano-pyrrole or to cyclohexadieno-pyrrole as examples of aromatic or partially hydrogentated aryl.

Important examples of heterocyclic ring systems as substituents which can also be benzo-fused are: indolyl, quinolyl, isoquinolyl, pyrazolyl, triazolyl, thiazolyl, oxazolyl, pyrimidinyl, imidazolyl, carbazolyl, pyridyl, thienyl or pyrazinyl.

The substituents mentioned, in particular the aromatic substituents, can be monosubstituted to pentasubstituted, depending on the number of H atoms which can be substituted, preferably monosubstituted to trisubstituted, for example by straight-chain or branched $C_1$-$C_6$-alkyl, $C_1$-$C_6$-alkoxy or $C_1$-$C_6$-alkylthio, or by hydroxyl, mercapto, halogen, carboxyl, sulfonyl, nitro, cyano, amino, $C_1$-$C_6$-alkyl-amino and di-($C_1$-$C_6$-alkyl)-amino, where the alkyl radicals can in turn be substituted by halogen, $C_1$-$C_4$-alkoxy, $C_1$-$C_4$-alkylthio, amino, alkylamino, hydroxyl, mercapto, carboxyl, sulfonyl or nitro.

$X^-$ as the anion equivalent is subject to no specific restriction; examples are: fluoride, chloride, bromide, iodide, azide, nitrite, nitrate, methoxy or the acetate anion, preferably chloride, bromide, hydroxyl or the acetate anion.

If $X_1$ to $X_4$ are identical and denote $CY_1$, $CY_2$, $CY_3$ or $CY_4$, where $Y_1$ to $Y_4$ have the abovementioned meaning, the compounds of the formula (V) are generally described as porphyrins. A large number of porphyrins have been synthesised by condensation of aldehydes with substituted or unsubstituted pyrrole. For example, meso-tetraphenylporphine is obtained by condensation of benzaldehyde with pyrrole (J. Org. Chem. 32, 476 (1967)). In similar manner, meso-tetra-n-propyl-porphine is obtained by condensation of pyrrole with n-butyraldehyde or octamethyl-porphine is obtained by reaction of formaldehyde with 3,4-dimethylpyrrole (Liebigs Ann. Chem. 718 (1968) 183-207). If the condensation of aldehyde and pyrrole is carried out using a mixture of various aldehydes and various 3,4-substituted pyrroles, macrocycles of the formula (V) can be obtained of the type in which both $X_1$ to $X_4$ and the four pyrrole rings can be differently substituted. Normally, porphyrin mixtures are obtained in such a synthesis. These mixtures can be used directly for chelates which can be employed according to the invention. However, the individual components can also be employed after their separation. The metallation of the porphyrins obtained in these syntheses is carried out by reaction with iron or manganese salts, for example in dimethylformamide (J. Inorg. Nucl. Chem. 32 (1970), 2443).

If, in the formula (V), $X_1$ to $X_4$ are identical and denote $CY_1$, $CY_2$, $CY_3$ or $CY_4$, where $Y_1$ to $Y_4$ have the abovementioned meaning, and if both radicals of each pyrrole ring are part of a carbocycle or heterocycle, the formula (V) describes a class of porphyrins whose basic structure is benzoporphyrin in which $X_1$ to $X_4$ denotes CH and each pyrrole ring is benzo-fused. Possible preparation routes for benzoporphyrin are the self-condensations of methylphthalimidine or o-cyano-cetophenone in the presence of magnesium (Liebigs ann. Chem. 533 (1938), 197). The desired iron or manganese benzoporphyrin can be obtained in principle by a suitable transmetallation process. In principle, a large variety of other porphyrins is accessible by analogous condensation of substituted o-cyano-aryl ketones. Such porphyrins can also additionally be meso-substituted.

If, in the formula (V), one or all of $X_1$ to $X_4$ denote N, the compounds are described, depending on the number of aza groups, as mono-, di-, tri-, and tetraazaporphyrins or generally as azaporphyrins. An exception is the tetrabenzo-tetraazaporphyrin known as phthalocyanine. Preparation possibilities for azaporphyrins and phthalocyanines, for example phthalocyanine, phthalocyanine tetrasulphonate, naphthalocyanine, tetrathiophenotetraazaporphine and octamethyltetraazaporphine can be inferred from the literature. Mono- di- and triazaporphyrins are accessible by similar routes, like the benzoporphyrins and tetraazaporphyrins. Mono- and diazaporphyrins can be obtained, for example, by heating a mixture of phthalonitrile, o-cyano-aryl ketone and metal salt according to Liebigs Ann. Chem. 531 (1937) 279, for example, by heating a mixture of phthalonitrile, methylenephthalimidene and metal salt (EP 0,003,149). A large variety of compounds of the formula (V) are accessible according to this method by suitable substitution on phthalonitrile or on o-cyano-aryl ketone, among them also those which are additionally meso-substituted.

Meso-tetraarylporphines are preferentially employed. The iron and manganese complexes of the meso-tetraarylporphines which can be employed according to the invention are represented by the formula

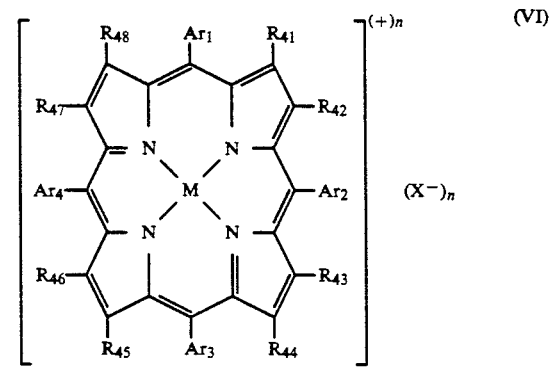

in which

M, $X^-$ and n have the above meaning, $R_{41}$, $R_{42}$, $R_{43}$, $R_{44}$, $R_{45}$, $R_{46}$, $R_{47}$ and $R_{48}$ independently of one another denote hydrogen, halogen or $C_1$-$C_4$-alkyl and in each case one of $R_{41}$ to $R_{48}$ per pyrrole nucleus can also be $C_7$-$C_{10}$-aralkyl or phenyl and $Ar_1$, $Ar_2$, $Ar_3$ and $Ar_4$ are independently of one another a carbocyclic or heterocyclic aromatic radical.

Porphyrins of the formula (VI) can be prepared in metal-free form, for example, by condensation of unsubstituted or suitably substituted pyrrole and correspondingly substituted arylaldehydes (J. Org. Chem. 32 (1967), 476). The metallation is carried out by reaction with iron or manganese salts, for example in dimethylformamide (J. Inorg. Nucl. Chem. 32 (1970), 2443). If mixtures of differently substituted pyrroles and mixtures of various arylaldehydes are employed in the condensation of pyrrole and arylaldehyde, porphyrins of the formula (VI) are obtained which can in each case be differently substituted both in the individual meso-positions and in the pyrrole moiety. Such porphyrins are normally obtained as mixtures of several porphyrins of varying composition. These porphyrin mixtures can be employed directly for the process according to the invention.

Examples of meso-tetraarylporphines which can be employed according to the invention and which form metal complexes of the formula (VI) are:
tetraphenylporphine
tetrakis-(2-methoxyphenyl)-porphine
tetrakis-(2,4-dimethoxyphenyl)-porphine
tetrakis-(2,3,4-trimethoxypehnyl)-porphine
tetrakis-(2-ethoxyphenyl)-porphine
tetrakis-(2-isopropoxyphenyl)-porphine
tetrakis-(2-bromophenyl)-porphine
tetrakis-(2,4-dimethylphenyl)-porphine
tetrakis-(2,6-dichlorophenyl)-porphine
tetrakis-(pentafluorophenyl)-porphine
tetrakis-(2-mercaptomethylphenyl)-porphine
tetrakis-(2-pyridyl)-porphine
tetrakis-(2-methylpyridinium)-porphine
tetrakis-(4-methylpyridinium)-porphine
tetrakis-(4-dimethylamino-2-methoxyphenyl)-porphine
tetrakis-(2-aminophenyl)-porphine
tetrakis-(2-phenyl-trimethylamonium-chloride)-porphine
tetrakis-(2-carboxyphenyl)-porphine
sodium tetrakis-(2-phenylsulfonate)-porphine
tetrakis-[-1-naphthyl]-porphine
tetrakis-(2-methoxy-1-naphthyl)-porphine
tetrakis-[-9-anthracenyl]-porphine
tetrakis-[2-(3-methylthiophenyl)]-porphine
tetrakis-(2-hydroxyphenyl)-porphine
tetrakis-(2-trifluoromethyl)-porphine
tetrakis-(2-hydroxy-4-methoxyphenyl)-porphine
tetrakis-(4-dimethylamino-2-hydroxyphenyl)-porphine
tetrakis-(2-mercaptophenyl)-porphine
tetrakis-(2-hydroxy-5-nitrophenyl)-porphine
tetrakis-[2-(2-hydroxyethoxy)-phenyl]-porphine
tetrakis-[2-(2-mercaptoethoxy)-phenyl]-porphine
tetrakis-[2-(2-methylmercaptoethoxy)-phenyl]-porphine
tetrakis-[2-(2-carboxyethoxy)-phenyl]-porphine
meso-tetrakis-(pentafluorophenyl)-octafluorophorphine
meso-tetraphenyl-octamethyl-porphine
tetrakis-[8-hydroxy-4-methoxy-1-naphthyl]-porphine
tetrakis-[8-hydroxy-7-quinolinyl]-porphine
tetrakis-[8-methoxy-7-quinolinyl]-porphine Among the meso-tetraaryl-porphines of the formula (VI), those are preferred whose aryl moiety is substituted at least in the 2-position. A substituent of this type in the 2-position can, for example, also be a fused carbocycle or heterocycle.

Examples of these preferred meso-tetraarylporphines are:
tetrakis-(2-methoxyphenyl)-porphine
tetrakis-(2-hydroxyphenyl)-porphine
tetrakis-(2,4-dimethoxyphenyl)-porphine
tetrakis-(2,3-dimethoxyphenyl)-porphine
tetrakis-(2-bromophenyl)-porphine
tetrakis-(2-ethoxyphenyl)-porphine
tetrakis-(2-fluorophenyl)-porphine
tetrakis-[8-hydroxy-7-quinolinyl]-porphine
tetrakis-(4-dimethylamino-2-hydroxyphenyl)-porphine In a manner familiar to the person skilled in the art, those coordination sites on the metal which are not occupied by the complex ligand are occupied by any desired donors, for example by ammonia, carbon monoxide, amines, such as pyridine, piperidine, imidazole, diethylamine, by sulphides, such as dimethylsulphide or dimethyl sulphoxide or by phosphorus compounds, such as tributylphosphine or tributyl phosphite. Such donors can also be added to the reaction mixture separately form the iron and/or manganese complex.

The iron and/or manganese complexes according to the invention can also be employed as dimers, oligomers or polymers. The dimerisation, oligomerisation or polymerisation can be effected, for example, by bridge formation between the metal centres or by crosslinking via the complex ligands. Examples of the use of the complexes according to the invention as dimers are the oxo-bridged metal-tetraaryl-porphines $(FeTAP)_2O$ and $(MnTAP)_2O$ (TAP= tetraarylporphine). Use in polymeric form can be carried out, for example, after crosslinking with a suitably functionalised polystyrene (J./Macromol. Sci. -Chem., A 25 (1988), 1126-36). The iron and/or manganese complex can furthermore also be employed in combination with a surface-active substance, for example in combination with active carbon.

The iron and/or manganese complexes employed according to the invention are surprisingly highly active, even in traces. The molar ratio of iron and/or manganese complex to o-cresol employed is 0.000001–0.05:1, preferably 0.00001–0.01:1. Of course, a larger amount of chelate complex than that indicated can be employed, however this offers no additional advantage, but only increases the costs and can make working-up difficult under certain circumstances.

The iron and/or manganese complexes are advantageously, but not necessarily, employed in the process according to the invention in combination with copper or a copper compound as a co-catalyst. The copper can assume the valencies 0, 1, 2 or 3, preferably 1 or 2, in the co-catalysts. Possible forms for use are the copper salts of inorganic acids, for example copper fluoride, copper chloride, copper bromide, copper iodide, copper sulphate, copper nitrate, basic copper carbonate, copper cyanide, copper phosphate, copper borate; the copper oxides; the copper salts of organic acids, such as copper acetate, copper oxalate, copper citrate, copper stearate; ion exchangers which contain copper; copper complexes, such as copper acetylacetonate, and N,N'-disalicylideneethylenediamine-copper(II). Copper salts can also be employed in combination with a complexing agent; complexing agents are, for example, ammonia, amines, such as ethylenediamine, and sulphides, such as dimethylsulphide. Even the use of elemental copper is effective, as already described above. In a preferred form, copper salts, both in hydrated and in anhydrous form, or copper oxide is employed, for example $CuCl_2.2H_2O$, $Cu(NO_3)_2.3H_2O$, $Cu(CH_3COO)_2.H_2O$, $CuSO_4.5H_2O$, CuO, CuCl.

Copper and copper compounds as co-catalysts also display their co-catalytic activity even in very small concentrations. Copper or a copper compound is employed in a molar ratio to o-cresol of 0.000001–0.1:1, preferably 0.00001–0.05:1.

Basically reacting substances suitable in the process according to the invention are all those which have a higher basicity than the o-cresolates which can be prepared therefrom, for example metal hydroxides, metal alkoxides and metal amides of alkali metals and alkaline earth metals and, if they are alcohoxides and amides, of aluminium. Important metals among those mentioned are, for example, sodium, potassium, lithium, calcium and magnesium. Examples of alkoxides which may be mentioned are the methoxide, the ethoxide, the isoproproxide and the tert.-butoxide. The amides can be, for example, the diethylamide, ethylamide, diisopropylamide, dibutylamide, etc. Among the bases mentioned, the hydroxides and the alkoxides are preferred; sodium hydroxide, potassium hydroxide, sodium methoxide, sodium ethoxide and potassium tert.-butoxide are particularly preferred.

The basic reacting substance is employed in an amount of 1-10 base equivalents per mol of the o-cresol; preferentially 1.5-6 base equivalents are employed.

Suitable solvents for the process according to the invention are those which do not react or only react very slowly with oxygen under the reaction conditions and which dissolve the o-cresols to be oxidised. Such solvents are, for example, alcohols, ethers, hydrocarbons, halogenated hydrocarbons, amines, amides and sulphoxides. Solvents of this type can be employed individually or in mixtures of two or more solvents. If these solvents are completely or partially miscible with water, mixtures of this type with water are also suitable. Preferentially, alcoholic solvents are employed such as methanol, ethanol, osopropanol, butanol, tert.-butanol and ethylene glycol. Methanol is very particularly preferred as a solvent.

In addition to the o-hydroxy-benzaldehydes (I), optionally substituted o-hydroxy-benzyl alcohols of the formula

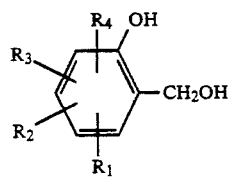

(VII)

are found in the reaction mixture and, if alcohols are used as solvents, also o-hydroxy-benzyl alkyl ethers of the formula

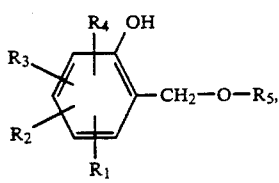

(VIII)

in which $R_1$ to $R_4$ have the abovementioned scope of meaning and $R_5$ is the alkyl radical of the alcohol used as the solvent.

$R_5$ is, for example, $C_1$-$C_4$-alkyl of the abovementioned type, preferably methyl.

The amount of these alcohols (VII) and ethers (VIII) varies somewhat with the reaction conditions. Both groups of substances can be recyclised in a subsequent batch and undergo therein a further oxidation to give the desired o-hydroxy-benzaldehydes.

Pure oxygen or oxygen in dilute form, for example in the form of oxygen-containing gases, can be employed as oxygen for the process according to the invention. The economically most favourable form of oxygen used according to the invention is atmospheric air. The pressure of the oxygen or of the oxygen-containing gas is subjected to no particular restriction and can be between 0.5 and 20 bar, preferably 0.8-10 bar, particularly preferably in the vicinity of atmospheric pressure. When using oxygen-containing gases, the oxygen content is likewise subjected to no restriction. The oxygen content depends above all on operational considerations, such as the avoidance of explosive mixtures of the solvent vapours. The content and the amount of oxygen furthermore depend on the reaction rate. It is advantageous to distribute the oxygen in the reaction mixture finely, for example using frits. However, the oxygen can also be absorbed into the reaction mixture by vigorous stirring using a suitable stirrer. The intensity of aeration, i.e. the amount of oxygen available per unit time can also vary greatly and depends, for example, on the removal of heat and on the reactivity of the o-cresol employed. The maximum absorption of oxygen and the most favourable reaction conditions, which may differ form this, can be determined by simple preliminary tests. In general, the reaction is advantageously carried out below the maximum oxygen absorption capacity of the reaction mixture.

The reaction temperature can vary within wide limits, for example from 0°-200° C., preferably 20°-150° C.

To work up the reaction mixture after completion of the absorption of oxygen, the catalyst and, if appropriate, the co-catalyst or a mixture of several of them are first removed, for example by filtering, centrifuging or decanting off. Catalysts and co-catalysts can be reused in a subsequent batch after their removal. Unreacted o-cresol and the alcohols (VII) and, if desired, the ethers (VIII) are also fed back into a subsequent batch.

A combination for advantageous reaction conditions which may be mentioned is: methanol as the solvent, sodium hydroxide, sodium methoxide, potassium hydroxide or a mixture of these as the basically reacting substance, iron- and/or manganese-tetrakis-(2,4-dimethoxyphenyl)-porphine chloride as the catalyst and $Cu(NO_3)_2.3H_2O$ as the co-catalyst.

The o-hydroxy-benzaldehyde obtained according to the invention is present in the reaction mixture as a metal salt, frequently as the sodium or potassium salt. This salt may be poorly soluble int e solvent, so that it is deposited as a precipitate. In this case, the working-up is carried out so that this metal salt of the o-hydroxy-benzaldehyde, if desired together with the catalyst and the co-catalyst, is removed by filtering, centrifuging or decanting off. The o-hydroxy-benzaldehyde is then liberated by acidifying and can be isolated by customary methods and, if desired, purified. The filtrate from the removal of the precipitated salt is worked up for unreacted cresol and for the alcohols (VII) or ethers (VIII). They ar reused in the manner described.

A further favourable working-up variant consists in spray-drying the reaction mixture, dissolving the soluble components of the dry residue in hot water and then filtering off the catalysts if desired. If the sodium or potassium salt of the o-hydroxy-benzaldehyde is poorly soluble in cold water, such an aqueous solution can be heated to 50°-90° C. and filtered at this temperature. The o-hydroxy-benzaldehyde is liberated from the aqueousalkaline solution by acidifying and separated, if desired, from unreacted o-cresol or from the alcohols (VII) and, if desired, the ethers (VIII). The o-hydroxybenzaldehyde can be separated and purified in a known manner by known methods, for example by fractional distillation or steam distillation or via adduct formation with bisulphite.

In the case mentioned where the sodium or potassium salt of the o-hydroxy-benzaldehyde is insoluble in aqueous alkali, the o-hydroxy-benzaldehyde can also be isolated form the aqueous-alkaline solution by removing the sodium or potassium salt of the o-hydroxy-benzaldehyde, for example by filtration. The o-hydroxy-benzaldehyde is then liberated fror the isolated sodium or potassium salt of the o-hydroxy-benzaldehyde by acidifying. The filtrate from the separation of the precipitated salt is in turn worked up for unreacted cresol and for the alcohols (VII) or the ethers (VIII).

In a still further working-up variant, 0.5-5 times the amount by weight of water, relevant to the solvent, is added to the reaction mixture, in particular if an alcoholic solvent has been used as the reaction medium, and the solvent is distilled off with the air of a column. The aqueous-alkaline distillation residue is then further worked up in the manner described.

EXAMPLE 1

A stream of oxygen of 1.0 l/h at normal pressure was passed into a mixture of 54.0 g (0.5 mol) of 2-cresol, 250 g of methanol, 100 g (2.5 mol) of sodium hydroxide, 66 mg (0.07 mmol) of iron-tetrakis-(2,4-dimethoxyphenyl)-porphine-chloride and 50 mg (0.2 mmol) of Cu(NO$_3$)$_2$.3H$_2$O in a 1 l reactor at 70° C. with vigorous stirring for 30 h.

The methanol was then distilled off, the residue was taken up in water and the product composition was determined by HPLC analysis of the resulting aqueous-alkaline solution.

| Yield (% of theoretical yield): | |
|---|---|
| 2-hydroxybenzaldehyde | 78.3% |
| 2-hydroxybenzyl methyl ether | 6.5% |
| 2-hydroxybenzyl alcohol | not found |
| 2-cresol | not found |

To isolate the products, the aqueous-alkaline solution was acidified to pH=2.5 and extracted three times with ethyl acetate. The ethyl acetate phases were combined, dried over sodium sulphate and the solvent was removed on a rotary evaporator. 72.8 g of a brown-coloured liquid having a content of 65.1% 2-hydroxybenzaldehyde and 4.2% 2-hydroxybenzyl methyl ether remained as a residue.

EXAMPLE 2

A stream of oxygen of 2.0 l/h at normal pressure was passed into a mixture of 54.0 g (0.5 mol) of 2-cresol, 250 g of methanol, 100 g (2.5 mol) of sodium hydroxide, 132 mg (0.14 mmol) of iron-tetrakis-(2,4-dimethoxyphenyl)-porphine-chloride in a 1 l reactor at 70° C. with vigorous stirring for 13 h.

Working-up was carried out as in Example 1.

| Yield (% of the theoretical yield) in the aqueous-alkaline solution: | |
|---|---|
| 2-hydroxybenzaldehyde | 39.6% |
| 2-hydroxybenzyl methyl ether | 14.2% |
| 2-hydroxybenzyl alcohol | not found |
| 2-cresol | not found |

EXAMPLE 3

Carrying-out as Example 2 with the difference that 108 mg of iron-tetrakis-(2-hydroxyphenyl)-porphine-chloride was employed as the catalyst.

| Yield (% of the theoretical yield) in the aqueous-alkaline solution: | |
|---|---|
| 2-hydroxybenzaldehyde | 60.3% |
| 2-hydroxybenzyl methyl ether | 13.9% |
| 2-hydroxybenzyl alcohol | 6.2% |
| 2-cresol | not found |

EXAMPLE 4

Carrying-out as Example 2 with the difference that the reaction was performed in the presence of 132 mg (0.14 mmol) of manganese-tetrakis-(2,4-dimethoxyphenol)-porphine chloride and 50 mg (0.2 mmol) of Cu(NO$_3$)$_2$.3H$_2$O as catalysts.

| Yield (% of the theoretical yield) in the aqueous-alkaline solution: | |
|---|---|
| 2-hydroxybenzaldehyde | 24.9% |
| 2-hydroxybenzyl methyl ether | 22.3% |
| 2-hydroxybenzyl alcohol | not found |
| 2-cresol | 21.6% |

EXAMPLE 5-10

Carrying-out took place as in Example 2 with the difference that 0.14 mmol of iron-tetraaryl-porphine chloride containing the tetraaryl-porphines specified in Table 1 together with 50 mg (0.2 mmol) of Cu(NO$_3$)$_2$.3H$_2$O were employed in each case as catalysts. The results are summarised in Table 1.

TABLE 1
(Examples 5-10)

| No. | Tetraarylporphine | Yield (% of theoretical yield) | | | |
|---|---|---|---|---|---|
| | | A | B | C | D |
| 5 | Tetrakis(2-methoxyphenyl)-porphine | 42.2 | 24.9 | 11.6 | 4.2 |
| 6 | Tetrakis-(2,3-dimethoxyphenyl)-porphine | 44.2 | 27.1 | — | — |
| 7 | Tetrakis-(2-ethoxyphenyl)-porphine | 46.1 | 26.6 | 6.9 | 1.6 |
| 8 | Tetrakis-(o-bromophenyl)-porphine | 24.0 | 23.2 | 12.2 | 11.4 |
| 9 | Tetrakis-[2-(3-methyl-thiophenyl)]-porphine | 10.1 | 21.3 | 18.5 | 38.4 |
| 10 | Tetrakis-[7-(8-hydroxy-quinolinyl)]-porphine | 46.8 | 21.9 | 13.6 | — |

A = 2-hydroxy-benzaldehyde;
B = 2-hydroxybenzyl methyl ether;
C = 2-hydroxy-benzyl alcohol;
D = 2-cresol.

EXAMPLE 11

A stream of oxygen of 2.0 l/h was passed at normal pressure into a mixture of 73.5 g (0.5 mol) of 4-chloro-2-methyl-phenol (97%), 250 g of methanol, 100 g (2.5 mol) of sodium hydroxide, 132 mg (0.14 mmol) of iron-tetrakis-(2,4-dimethoxyphenyl)-porphine chloride and 50 mg (0.2 mmol) of Cu(NO$_3$)$_2$·3H$_2$O in a 1 l reactor at 70° C. with vigorous stirring for 18 h.

The methanol was then distilled off under reduced pressure, the residue was taken up in water and the product composition was determined by HPLC analysis of the resulting aqueous-alkaline solution.

| Yield (% of theoretical yield): | |
| --- | --- |
| 5-chloro-2-hydroxybenzaldehyde | 44.2% |
| 5-chloro-2-hydroxbenzyl methyl ether | 23.7% |
| 4-chloro-methylphenol | not found |

EXAMPLE 12

Carrying-out as in Example 9 with the difference that 2,3-dimethylphenol was employed as the 2-cresol derivative.

| Yield (% of theoretical yield): | |
| --- | --- |
| 6-methyl-2-hydroxybenzaldehyde | 32.8% |
| 6-methyl-2-hydroxybenzyl methyl ether | 24.1% |
| 2,3-dimethylphenol | not found |

What is claimed is:

1. A process for the preparation of o-hydroxybenzaldehydes of the formula

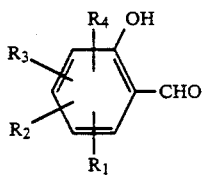

in which
R$_1$, R$_2$, R$_3$ and R$_4$ independently of one another denote hydrogen, straight-chain or branched C$_1$–C$_{10}$-alkyl, C$_3$–C$_8$-cycloalkyl, straight-chain or branched C$_1$–C$_{10}$-alkoxy, phenyl or halogen, provided that alkyl or cycloalkyl occupy the position para to the hydroxy group only if they carry no α-H-atoms,
by catalytic oxidation of o-cresols of the formula

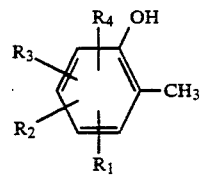

in which
R$_1$, R$_2$, R$_3$ and R$_4$ have the meanings indicated above. with oxygen in the presence of substances having a basic reaction, in a solvent, at a temperature of 0° to 200° C., and in the presence of a catalyst that is a chelate complex of (1) iron, manganese, or a mixture of iron and manganese with (2) a chelating agent which is a meso-tetraarylporphine whose aryl groups are substituted at least in the 2-position.

2. The process according to claim 1, wherein the molar ratio of iron and/or manganese complex to o-cresol is 0.000001–0.05:1.

3. The process according to claim 2, wherein the molar ratio of iron and/or manganese complex to o-cresol is 0.0000–0.01:1.

4. The process according to claim 1, wherein copper or a copper compound is employed as a co-catalyst to the chelate complex in a molar ratio to the o-cresol of 0.000001–0.1:1.

5. The process according to claim 4, wherein copper or a copper compound is employed as a co-catalyst to the chelate complex in a molar ratio to the o-cresol of 0.000001–0.1:1.

6. The process according to claim 1, wherein as substances having a basic reaction, one or more from the group comprising the hydroxides, alkoxides and amides of alkali metal and alkaline earth metals and alkoxides and amides of aluminium are employed in an amount of 1–10 base equivalents per mol of o-cersol.

7. The process according to claim 6, wherein as substances having a basic reaction, one or more from the group comprising the hydroxides, alkoxides and amides of alkali metal and alkaline earth metals and alkoxides and amides of aluminium are employed in an amount of 1.5–6 base equivalents per mol of o-cresol.

8. The process according to claim 1, wherein as solvents, one or more is employed form the group comprising the alcohols, ethers, hydrocarbons, halogenohydrocarbons, amines, amides and sulphoxides.

9. The process according to claim 8, wherein as solvents, one ore more alcohols are employed.

10. The process according to claim 9, wherein as a solvent methanol is employed.

11. The process according to claim 1, wherein the catalyst is a chelate complex of the formula

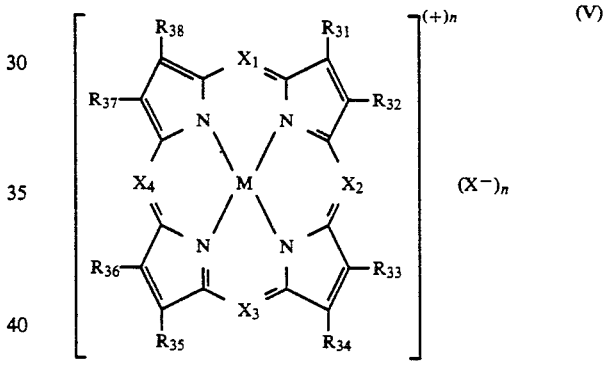

in which
M represents iron or manganese;
X$_1$, X$_2$, X$_3$ and X$_4$ independently represent N or CY$_1$, CY$_2$, CY$_3$ or CY$_4$, where Y$_1$, Y$_2$, Y$_3$, and Y$_4$ independently represent hydrogen, straight-chain or branched C$_1$–C$_{10}$-alkyl, C$_3$–C$_8$-cycloalkyl, C$_7$–C$_{10}$-aralkyl, C$_6$–C$_{14}$-aryl, which can be partially hydrogenated, or an aromatic or non-aromatic 5- or 6-membered heterocyclic ring system having 1 to 3 heteroatoms from the group consisting of N, O, and S;
R$_{31}$, R$_{32}$, R$_{33}$, R$_{34}$, R$_{35}$, R$_{36}$, R$_{37}$, and R$_{38}$ independently of one another represent hydrogen, halogen, straight-chain or branched C$_1$–C$_{10}$-alkyl, C$_3$–C$_8$-cycloalkyl, C$_7$–C$_{10}$-aralkyl or phenyl, or R$_{31}$ and R$_{32}$ or R$_{33}$ and R$_{34}$ or R$_{35}$ and R$_{36}$ or R$_{37}$ and R$_{38}$, together with the C atoms to which they are attached, can form C$_6$–C$_{14}$-aryl, which can be partially hydrogenated, or can form an aromatic or non-aromatic 5- or 6-membered heterocyclic ring system having 1 to 3 heteroatoms from the group consisting of N, O, and S;
X$^-$ represents an anion equivalent of an inorganic or organic acid, or hydroxyl or alkoxy; and
n represents the number 0 or 1.

* * * * *

UNITED STATES PATENT AND TRADEMARK OFFICE
CERTIFICATE OF CORRECTION

PATENT NO. : 5,130,493
DATED : July 14, 1992
INVENTOR(S) : Schnatterer et al.

It is certified that error appears in the above-indentified patent and that said Letters Patent is hereby corrected as shown below:

Col. 14, line 22, delete " ore " and substitute -- or --

Signed and Sealed this

Fourteenth Day of December, 1993

Attest:

BRUCE LEHMAN

*Attesting Officer*    *Commissioner of Patents and Trademarks*